United States Patent [19]
Lichtenwalner et al.

[11] Patent Number: 6,006,163
[45] Date of Patent: Dec. 21, 1999

[54] ACTIVE DAMAGE INTERROGATION METHOD FOR STRUCTURAL HEALTH MONITORING

[75] Inventors: Peter F. Lichtenwalner, St. Charles; James P. Dunne, Valley Park; Ronald S. Becker, St. Louis; Erwin W. Baumann, Florissant, all of Mo.

[73] Assignee: McDonnell Douglas Corporation, St. Louis, Mo.

[21] Appl. No.: 08/929,468

[22] Filed: Sep. 15, 1997

[51] Int. Cl.$^6$ .................................................. G01H 11/08
[52] U.S. Cl. .............................. 702/36; 702/34; 702/35; 73/583; 73/579
[58] Field of Search ................................ 702/33–36, 39, 702/42, 43, 56, 75–77, 103, 109–116, 170, 171, 179, 180, 183–185, 191, FOR 166, FOR 134, FOR 139, FOR 148, FOR 107, FOR 108; 364/528.1, 528.15; 395/500.27–500.29; 248/638, 562, 542, 550; 367/13, 901; 381/71.2, 71.9, 71.7, 71.11, 71.12; 244/75 R, 76 R, 1 N, 117 R; 310/328, 326, 332, 311, 313 R, 327, 320–322, 358, 369; 73/1.82, 865.6, 866, 1.48, 577–579, 582, 583, 588, 598, 600, 659, 660, 662–664, 602, 760, 767–769, 778, 786, 788, 789, 799, 801, 802, 804

[56] References Cited

U.S. PATENT DOCUMENTS

| | | | |
|---|---|---|---|
| 4,061,017 | 12/1977 | Sloane et al. | 73/664 |
| 5,163,015 | 11/1992 | Yokota | 395/500.28 |
| 5,195,046 | 3/1993 | Gerardi et al. | 702/35 |
| 5,327,358 | 7/1994 | Stubbs | 702/36 |
| 5,665,913 | 9/1997 | Chung | 73/583 |

OTHER PUBLICATIONS

Chaudhry et al., "Local health monitoring of aircraft via piezolelectric actuator/sensor patches", SPIE, vol. 2443, pp. 268–276 (1995).

Chaudhry et al., "Monitoring the Integrity of Composite Patch Structural Repair via Piezoelectric Actuators/Sensors," 36th AIAA/ASMEI ASCHE/AHS/ASC Conference, Apr. 10–13, 1995, pp. 2243–2248.

(List continued on next page.)

Primary Examiner—Hal Wachsman
Attorney, Agent, or Firm—Westerlund & Powell; Robert A. Westerlund; Raymond H. J. Powell, Jr.

[57] ABSTRACT

An active damage interrogation (ADI) system (and method) which utilizes an array of piezoelectric transducers attached to or embedded within the structure for both actuation and sensing. The ADI system actively interrogates the structure through broadband excitation of the transducers. The transducer (sensor) signals are digitized and the transfer function of each actuator/sensor pair is computed. The ADI system compares the computed transfer function magnitude and phase spectrum for each actuator/sensor pair to a baseline transfer function for that actuator/sensor pair which is computed by averaging several sets of data obtained with the structure in an undamaged state. The difference between the current transfer function and the baseline transfer function for each actuator/sensor pair is normalized by the standard deviation associated with that baseline transfer function. The transfer function deviation for each actuator/sensor pair is then represented in terms of the number of standard deviations, or sigmas, from the baseline. This statistic, termed the TF Delta, is then processed by a windowed local averaging function in order to reduce minor variations due to random noise, etc. The Windowed TF Delta for each actuator/sensor pair is then integrated over the entire excitation frequency spectrum, to thereby produce the Cumulative Average Delta, which provides a single metric for assessing the magnitude of change (deviation from baseline) of that particular actuator/sensor transfer function. The Cumulative Average Delta (CAD) for each actuator/sensor transfer function provides key, first-level information which is required for detecting, localizing, and quantitatively assessing damage to the structure.

45 Claims, 13 Drawing Sheets

OTHER PUBLICATIONS

Mitrovic et al., "Influence of Damage On the Vibration Response of Composite Laminates", ASME IMECE, Nov. 1995, pp. 1–9.

Castanien et al., "Application of active structural health monitoring technique to aircraft fuselage structures", Proceedings, SPIE Symposium on Smart Structures and Materials, vol. 2721, pp. 38–49, 1996 (no month).

NOTE: THE CUMULATIVE AVERAGE DELTA (CAD) RESULTS SHOWN ABOVE WERE OBTAINED FROM AN ACTUAL TEST OF ADI SYSTEM AFTER INTENTIONALLY PRODUCING A DEGRADED BOND IN SENSORS 5 AND 8 BY FLEXING THE MD EXPLORER FLEXBEAM TEST ARTICLE.

NOTE: THE CUMULATIVE AVERAGE DELTA (CAD) RESULTS SHOWN ABOVE WERE OBTAINED FROM AN ACTUAL TEST OF ADI SYSTEM AFTER INTENTIONALLY PRODUCING A DEGRADED BOND IN SENSORS 5 AND 8 BY FLEXING THE MD EXPLORER FLEXBEAM TEST ARTICLE.

ADI SYSTEM DAMAGE ASSESSMENT RESULTS

NO DAMAGE

SMALL DETAMINATION-ZONE 3

SMALL DETAMINATION-ZONE 3
LARGE DETAMINATION-ZONE 2

SMALL DETAMINATION-ZONE 3
LARGE DETAMINATION-ZONE 2
MEDIUM DETAMINATION-ZONE 1

ACTIVE DAMAGE INTERROGATION METHOD FOR STRUCTURAL HEALTH MONITORING

BACKGROUND OF THE INVENTION

The present invention relates generally to structural health monitoring methods and systems, and more particularly, to a structural health monitoring technique which actively interrogates the structure through broadband excitation of an array of piezoelectric transducers attached to or embedded within the structure for both actuation and sensing. Statistical analysis of the changes in transfer functions between actuator/sensor pairs is used to detect, localize, and assess the severity of damage in the structure.

A significant area of ongoing research and development efforts in the aerospace industry is the implementation of an automated structural health monitoring system (SHMS) using smart sensors and actuators integrated into the structure of an aerospace vehicle in order to provide a "built-in-test" (BIT) diagnostic capability for the structure. Such "smart structures" facilitate a reduction of acquisition and life cycle costs of aerospace vehicles which incorporate the same. A reliable SHMS will enable the practice of condition-based maintenance (CBM), which can significantly reduce life cycle costs by eliminating unnecessary inspections, minimizing inspection time and effort, and extending the useful life of new and aging aerospace structural components.

A principal requirement of an integrated SHMS is to provide a first level, qualitative damage detection, localization, and assessment capability which can signal the presence of structural damage and roughly localize the area where more precise quantitative non-destructive evaluation of the structure is needed.

Previous SHMS devices have primarily relied upon "passive" strain tracking or acoustic emission monitoring techniques, both of which have serious drawbacks and shortcomings. More particularly, both of these structural health monitoring techniques require continuous monitoring of the structure under evaluation in order to detect any damage to the structure. Thus, if a power failure (or power shut-down) occurs, the SHMS device is disabled. Further, the accuracy and reliability of the acoustic emission monitoring technique is compromised by the generally noisy environment of the aerospace vehicle. Another major disadvantage of acoustic emission (AE) monitoring is that a significant amount of data storage is required. The strain tracking technique requires the costly development of a finite element strain distribution model against which to compare the measured strain distribution across the structure in order to quantify and localize the damage. Moreover, both of these structural health monitoring techniques are severely limited with respect to their sensitivity, i.e., their ability to detect structural damage at the smallest possible level.

The most promising structural health monitoring techniques currently under development involve the use of piezoelectric transducers to actively excite and sense the vibration characteristics of the structure. This vibration signature is then compared with that of a normal undamaged structure and the difference is used to extract a metric related to the health of the structure. These structural health monitoring techniques can thus be regarded as "active" vibration-based structural health monitoring techniques.

Chaudhry et al. have demonstrated the use of piezoelectric transducers for local-area damage detection in metallic structure bond lines and joints, as well as in composite repair patches for metallic structures. See, Z. Chaudhry, T. Joseph, F. Sun, and C. Rogers, "Local-area health monitoring of aircraft via piezoelectric actuator/sensor patches,", *Proceedings, SPIE Symposium on Smart Structures and Materials*, Vol. 2443, pp. 38–49, 1995; and, Z. Chaudhry, F. Lalande, A. Ganino, and C. Rogers, "Monitoring the integrity of composite patch structural repair via piezoelectric actuators/sensors", *Proceedings, 36th AIAA/ASME/ASCE/AHS/ASC Structures, Structural Dynamics and Materials Conference*, pp. 2243–2248, 1995, the disclosures of which are incorporated herein by reference. Their technique utilizes a single piezoelectric transducer made of Lead Zirconate Titanate (PZT) bonded to the structure to obtain electrical impedance measurements across a specific frequency range using simultaneous actuation and sensing. Since the PZT provides a coupling between mechanical impedance and electrical impedance, vital mechanical impedance information of the structure can be extracted from the electrical impedance measurements. Damage to the structure affects the vibration signature of the structure. Thus, damage can be detected by monitoring the appropriate frequency spectrum of the electrical impedance function. Chaudhry et al. have demonstrated that de-bonds as small as ¼" in the composite patch produce a noticeable change in the impedance function at frequencies between 10 kHz and 20 kHz.

Castanien and Liang have extended this technique to include the cross-electromechanical impedance between pairs of PZT transducers to aid in monitoring a larger area of the structure while still providing some localization capability. See, K. E. Castanien and C. Liang, "Application of active structural health monitoring technique to aircraft fuselage structures", *Proceedings, SPIE Symposium on Smart Structures and Materials*, Vol. 2721, pp. 38–49, 1996, the disclosure of which is incorporated herein by reference. They have used this technique to demonstrate detection and localization of rivet line failures in a section of metallic aircraft fuselage using a frequency spectrum of 0 to 2 kHz.

Another "active" vibration-based structural health monitoring technique is disclosed in U.S. Pat. No. 5,327,358. However, the technique disclosed in this patent requires a model of the structure under evaluation, and thus, requires a priori information about the structure (including structural material and geometric properties) for deriving the model parameters.

Although the above-described vibration-based "active" structural health monitoring techniques are promising, they do not provide any mechanism for processing the information they obtain in order to facilitate accurate quantitative assessment and localization of any detected damage to the structure under evaluation. Further, their detection sensitivity and localization capabilities are limited, e.g., with respect to composite structure delamination damage.

Based on the above and foregoing, it can be appreciated that there presently exists a need in the art for a model-independent structural health monitoring system and method which overcomes the above-described drawbacks and shortcomings of the presently available technology. The present invention fulfills this need in the art.

SUMMARY OF THE INVENTION

The present invention encompasses an active damage interrogation (ADI) system (and method) which utilizes an array of piezoelectric transducers attached to or embedded within the structure for both actuation and sensing. The ADI system provides the ability to detect, localize, and estimate the severity of damage to the structure by actively exciting the structure with PZT transducers and processing the structural response as measured by the PZT transducers. The ADI system makes use of both amplitude and phase information from the various actuator/sensor transfer functions, and also provides a unique method for determining when the transducer/structure bond has degraded.

The ADI system actively interrogates the structure through broadband excitation of the transducers. The transducer (sensor) signals are digitized and the transfer function of each actuator/sensor pair is computed. The ADI system compares the computed transfer function magnitude and phase spectrum for each actuator/sensor pair to a baseline transfer function for that actuator/sensor pair which is computed by averaging several sets of data obtained with the structure in an undamaged state. The difference between the current transfer function and the baseline transfer function for each actuator/sensor pair is normalized by the standard deviation associated with that baseline transfer function, by utilizing well-known statistical analysis techniques. The transfer function deviation for each actuator/sensor pair is then represented in terms of the number of standard deviations, or sigmas, from the baseline. This statistic, termed the TF Delta, is then processed by a windowed local averaging function in order to reduce minor variations due to random noise, etc. The Windowed TF Delta for each actuator/sensor pair is then integrated over the entire excitation frequency spectrum, to thereby produce the Cumulative Average Delta, which provides a single metric for assessing the magnitude of change (deviation from baseline) of that particular actuator/sensor transfer function. The Cumulative Average Delta (CAD) for each actuator/sensor transfer function provides key, first-level information which is required for detecting, localizing, and quantitatively assessing damage to the structure. The CAD values for all actuator/sensor pairs can then be combined in order to obtain a composite damage indication metric for each actuator. The damage is then localized to a damage zone by identifying the actuator with the highest composite damage indication metric or damage index (DI). Further processing of an array of DI values can be performed to farther localize the damage within the identified damage zone.

BRIEF DESCRIPTION OF THE DRAWINGS

These and other objects, features, and advantages of the present invention will be readily understood from the following detailed description read in conjunction with the accompanying drawings, in which.

DETAILED DESCRIPTION OF THE INVENTION

Figure 1:
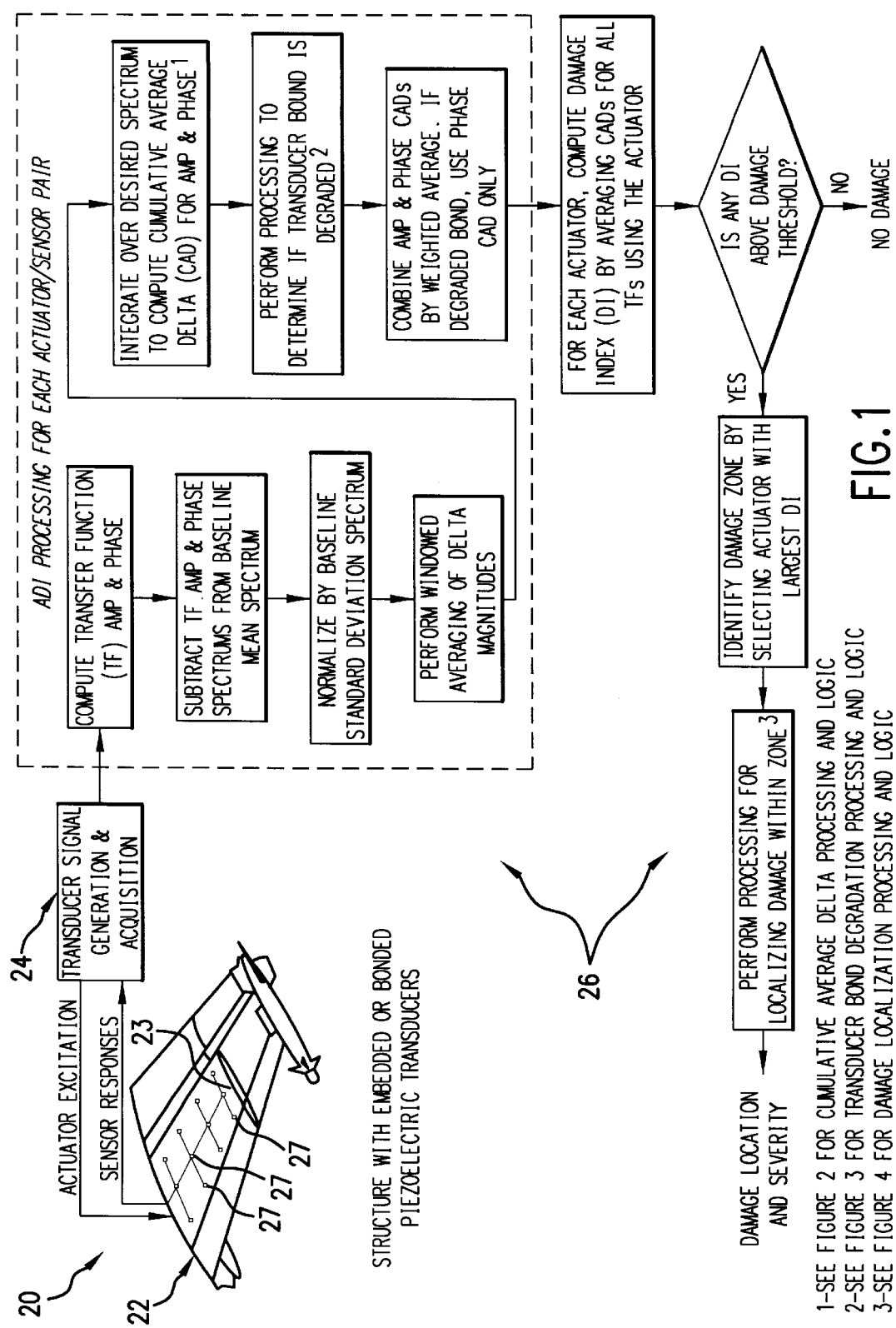
FIG. 1 is a block diagram of an ADI system according to an exemplary embodiment of the present invention.

In overview, the present invention is directed to an active damage interrogation (ADI) system (and method) which utilizes an array of piezoelectric transducers attached to or embedded within the structure for both actuation and sensing. The ADI system actively interrogates the structure through broadband excitation of the transducers. The transducer (sensor) signals are digitized and the transfer function (TF) amplitude and phase of each actuator/sensor pair is computed. The ADI system compares the computed transfer function magnitude and phase spectrum for each actuator/sensor pair to a baseline transfer function for that actuator/sensor pair which is computed by averaging several sets of data obtained with the structure in an undamaged state. The difference between the current transfer function and the baseline transfer function for each actuator/sensor pair is normalized by the standard deviation associated with that baseline transfer function, by utilizing well-known statistical analysis techniques.

The transfer function deviation for each actuator/sensor pair is then represented in terms of the number of standard deviations, or sigmas, from the baseline. This statistic, termed the TF Delta, is then processed by a windowed local averaging function in order to reduce minor variations due to random noise, etc. The Windowed TF Delta for each actuator/sensor pair is then integrated over the entire excitation frequency spectrum, to thereby produce the Cumulative Average Delta (CAD), which provides a single metric for assessing the change (deviation from baseline) in transfer function amplitude and phase for each actuator/sensor transfer function. It will be noted that this statistic (CAD) is somewhat similar to the "Sumdelta" statistic used by Mitrovic et al. for detecting delaminations in a composite panel. See, M. Mitrovic, G. P. Carman, G. A. Hickman, and Y. Bar-Cohen, "Influence of damage on the vibration response of composite laminates", *ASME International Mechanical Engineering Congress & Exposition,* 1995, the disclosure of which is incorporated herein by reference. However, there is a significant difference. More particularly, the Mitrovic et al. "Sumdelta" statistic represents the percent difference in the measured power spectral density from the baseline for a particular sensor, whereas the CAD statistic in the present invention represents the difference between the transfer function phase and amplitude.

By using both amplitude and phase information, the present invention achieves greater damage detection sensitivity as well as the ability to detect transducer/structure bond degradation and to discriminate between damage to the composite structure and transducer/structure bond degradation. Also, the CAD statistic in the present invention is normalized by the baseline standard deviation, and is thus represented in terms of the number of standard deviations from the baseline. This provides compensation for different signal-to-noise conditions in the structure and the transducers.

The Cumulative Average Delta (CAD) for each actuator/sensor transfer function provides key, first-level information which is required for detecting, localizing, and quantitatively assessing damage to the structure. The CAD values for all actuator/sensor pairs can then be combined in order to obtain a composite damage indication metric for each actuator. The damage is then localized to a particular damage zone by identifying the actuator with the highest composite damage indication metric or damage index (DI).

It will be noted that the individual actuator/sensor transfer functions provide essentially the same information as that of the cross-electromechanical impedance functions between pairs of PZT transducers obtained using the previously discussed Castanien and Liang technique, but can be computed much easier and using less costly equipment. More importantly, Castanien and Liang (and all others working in the field) perform only limited statistical processing of the transfer function information. Consequently, these techniques are quite vulnerable to sensor and system noise and degraded transducer/structure bonds, and thus, do not provide a complete mechanism for accurately localizing and quantitatively assessing any detected damage to the structure, or for detecting transducer/structure bond degradation or discriminating between damage to the composite structure and transducer/structure bond degradation. Moreover, none of these systems have been demonstrated to be capable of detecting very small (e.g., ¼" diameter) internal delaminations, as has the ADI system of the present invention.

Essentially, the presently available active structural health monitoring techniques only provide a qualitative damage assessment tool which has limited detection sensitivity and localization capability. The present invention greatly extends the capability of the presently available technology by facilitating highly sensitive, accurate, and reliable detection of damage to the structure, as well as much more precise localization and quantitative assessment of the damage. Moreover, by comparing both the magnitude and phase of the actuator/sensor transfer functions with the corresponding baseline transfer functions, a much greater ability to discriminate between damage to the structure and degraded transducer-to-structure bonding (or other transducer damage) is realized, thus significantly enhancing the overall accuracy and reliability of the system.

With reference now to FIG. 1, a block diagram of the ADI system 20 of the present invention is presented. As can be seen, the ADI system 20 includes actuator/sensor instrumentation 22 which is embedded or attached to the structure 23 under evaluation, a transducer signal generation and data acquisition system 24, and an ADI processing section 26.

The number, type, and location of the transducers (actuators and/or sensors) 27 employed in the actuator/sensor instrumentation 22 is not limiting to the present invention, in its broadest sense. In this regard, the actuator/sensor instrumentation 22 can suitably be of the same or similar configuration as any of those disclosed in the previously discussed references which have been incorporated herein by reference. In the preferred embodiment, the actuators and sensors 27 are piezoelectric (PZT) transducers which can be used for both actuation and sensing.

The transducer signal generation and data acquisition system 24 preferably includes an excitation signal source and a commercial off-the-shelf (COTS) plug-in analog-to-digital data acquisition board, both of which are electrically coupled to the actuator/sensor instrumentation 22.

The ADI processing section 26 preferably includes a microprocessor or computer (e.g., a PC) and appropriate software for executing the necessary computational and statistical processing algorithms. For example, in an experimental laboratory setup of the ADI system 20 MATLAB software from The Math Works, Inc., was used on a PC platform. Of course, the hardware can be miniaturized and ruggedized for field implementation, e.g., for ground-based field testing of instrumented structures.

During operation, the ADI system 20 uses broadband random (white noise) excitation (or alternatively, chirp excitation) to actuate the transducers of the actuator/sensor instrumentation 22 over a frequency range of 0 to 100 kHz, although these operating parameters are not limiting to the present invention, in its broadest sense. The analog signals produced by the sensors of the actuator/sensor instrumentation 22 in response to this excitation (i.e., "sensor response") are digitized by the data acquisition system 24. The transfer function (TF) amplitude and phase for each sensor of the actuator/sensor instrumentation 22 is then computed by the ADI processing section 26 via the Fast Fourier Transform (FFT).

Figure 2:
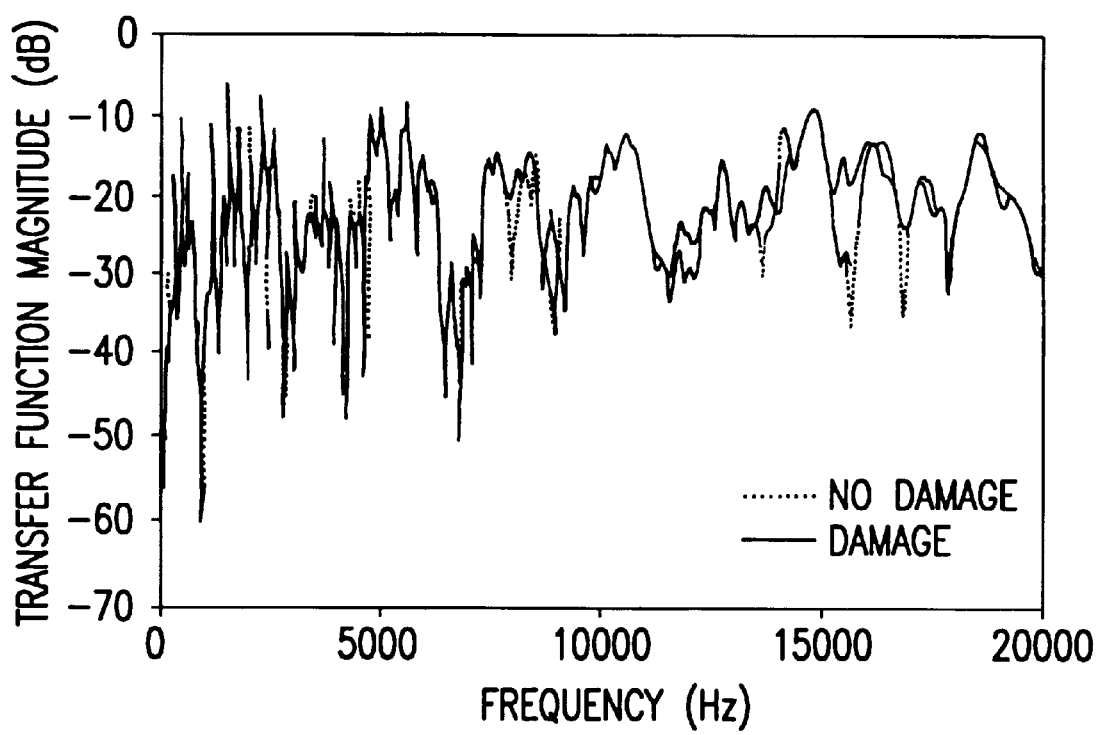
FIG. 2 depicts the transfer function magnitude spectrums for both "damage" and "no damage" conditions of a structure evaluated in an experiment conducted with an experimental laboratory setup of the ADI system of the present invention.
Figure 3A:
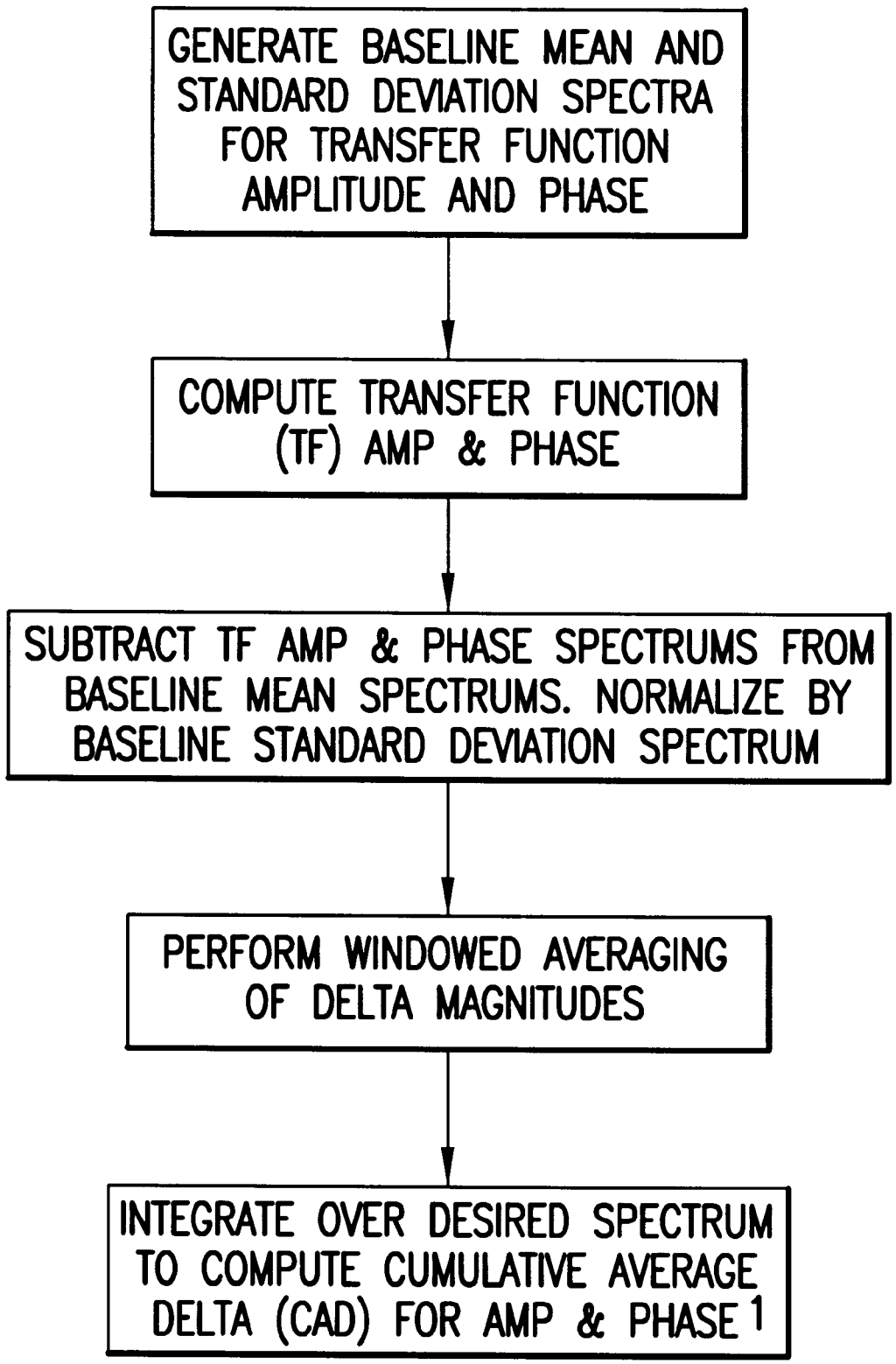
FIG. 3 depicts the processing logic for obtaining the Cumulative Average Delta (CAD) statistic used in the ADI system of the present invention.
Figure 3B:
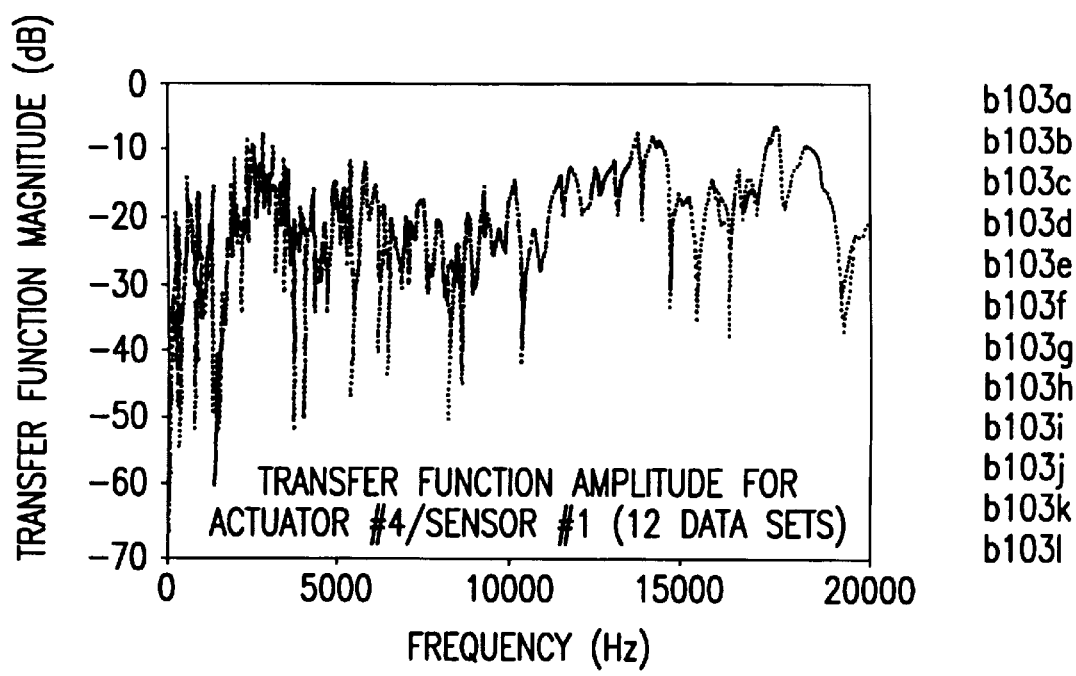
Figure 3C:
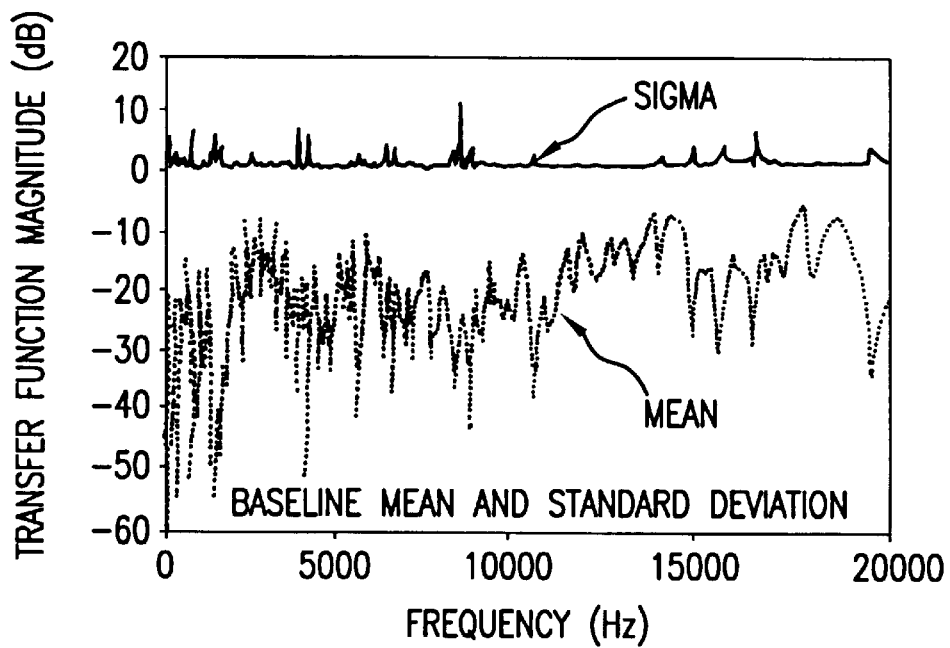
Figure 3D:
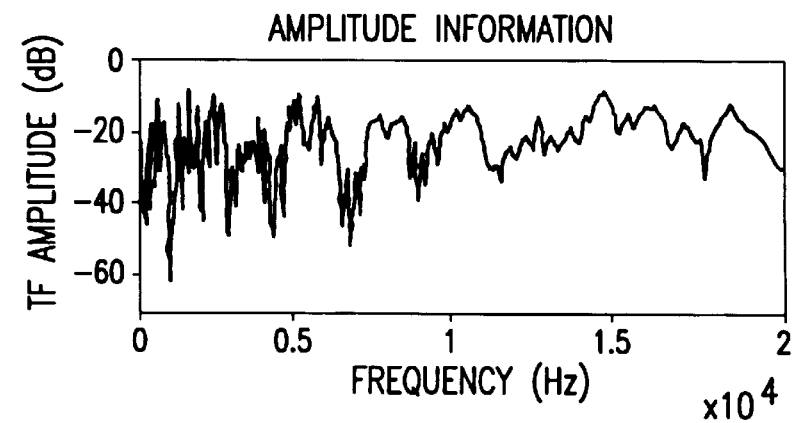
Figure 3E:
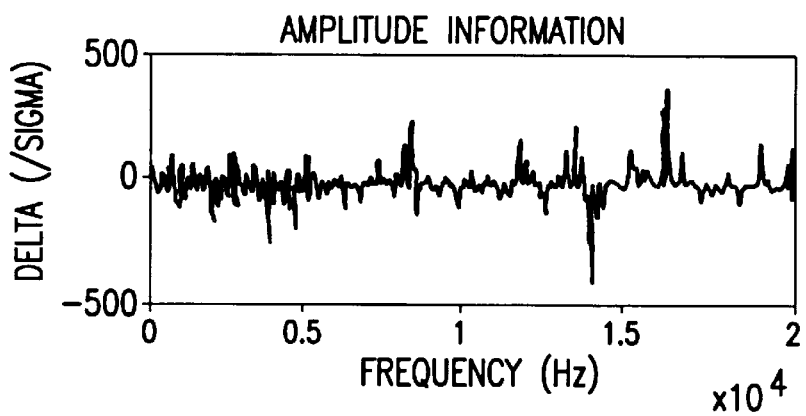
Figure 3F:
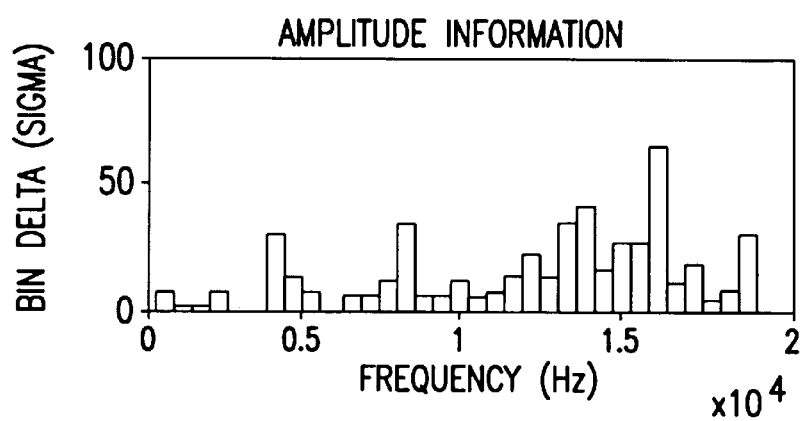
Figure 3G:
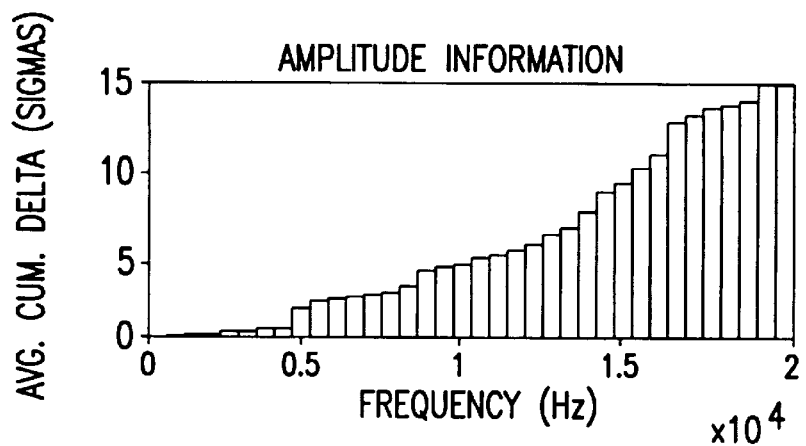
Figure 3H:
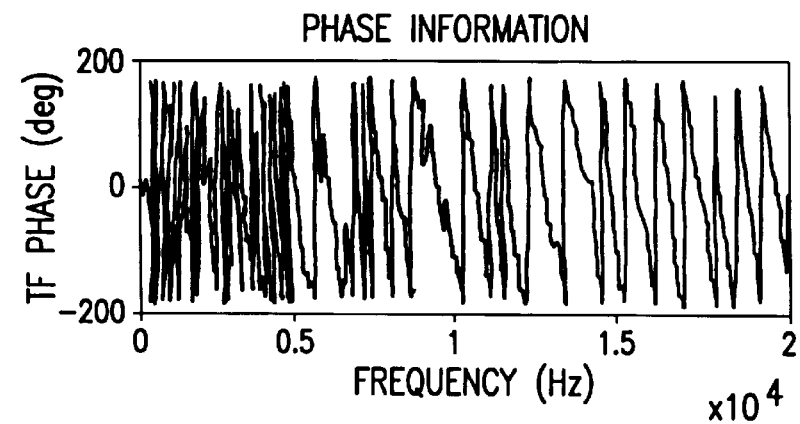
Figure 3I:
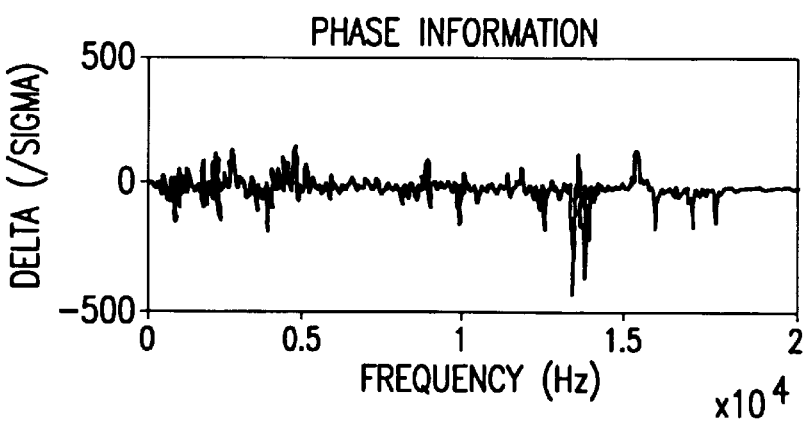
Figure 3J:
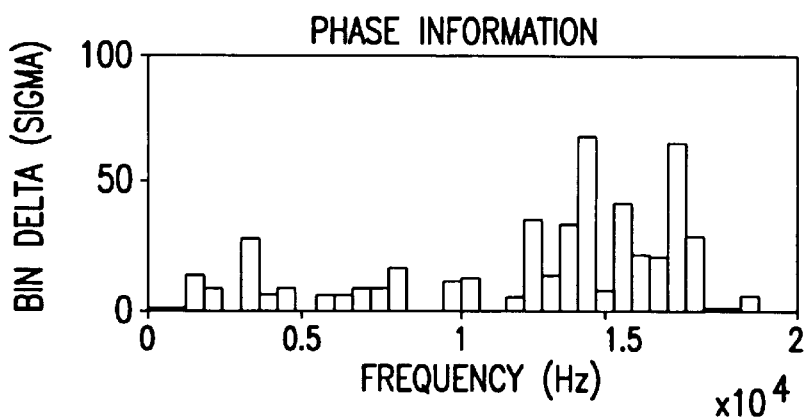
Figure 3K:
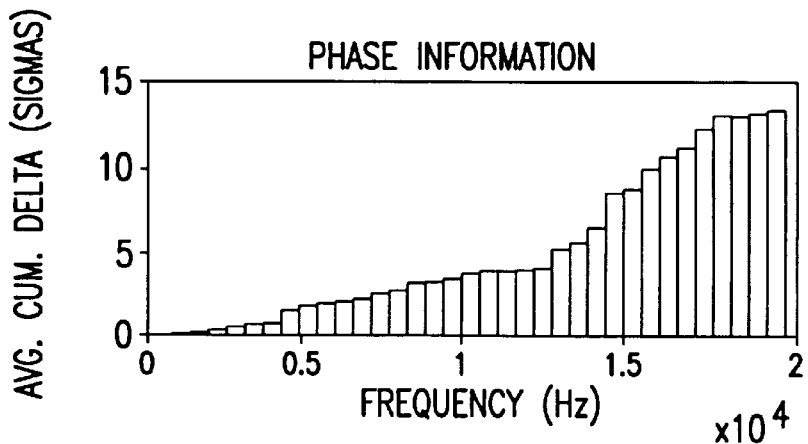

The vibration signature of the structure under evaluation is then computed via the transfer function for each sensor of the actuator/sensor instrumentation 22. Peaks in the transfer function magnitude spectrum represent global structural modes at lower frequencies and local structural resonances at higher frequencies. Damage such as small cracks and delaminations produce measurable changes in the structure's vibration signature. An example of this measurable change is illustrated in FIG. 2, which depicts the transfer function magnitude spectrums for both "damage" and "no damage" conditions of a structure evaluated in an experiment conducted with an experimental laboratory setup of the ADI system 20 to be discussed hereinafter.

The ADI processing section 26 then performs the statistical processing of the transfer function information discussed hereinabove in order to produce the Cumulative Average Delta for each sensor of the actuator/sensor instrumentation 22, as is graphically depicted in FIG. 3. The CAD values for all actuator/sensor pairs can then be combined in order to obtain a composite damage indication metric or damage index (DI) for each actuator. The damage is then localized to a particular damage zone by identifying the actuator with the highest DI. The ADI processing section 26 then performs further processing for further localizing the identified damage zone.

Figure 4:
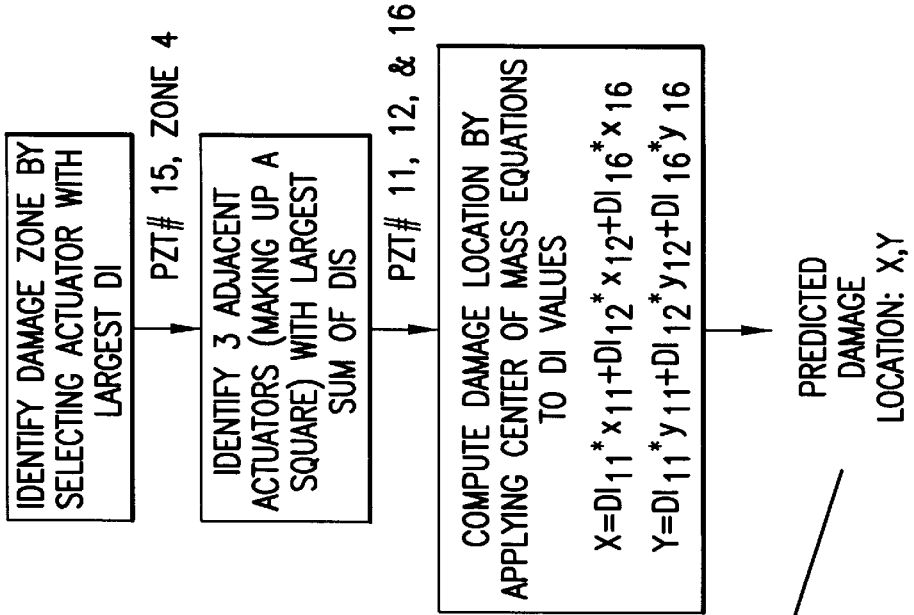
FIG. 4 depicts a damage localization algorithm used in a preferred embodiment of the ADI system of the present invention.
Figure 4:
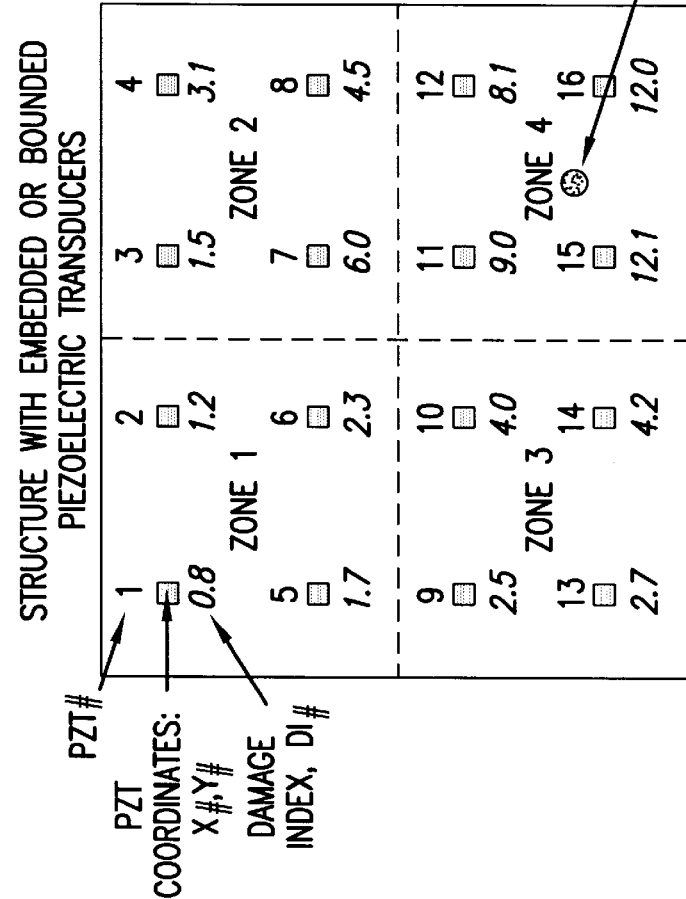

A presently preferred damage localization algorithm is presented in FIG. 4. As discussed above, the first step in localizing damage is to compute the DI for each actuator. This involves averaging the CAD values for each transfer function which uses this actuator, to obtain a single metric for each actuator. The actuator with the highest DI is used to identify the damage zone, according to a predefined division of the structure into various zones according to its load bearing behavior or inspection requirements. The location of damage within the identified damage zone, or for smaller structures which are not subdivided into different zones, can then be further pinpointed by processing an array of DI values. Using the actuator with the highest DI as one corner, the three adjacent actuators which make up a rectangular grid and provide the largest sum of DI values are identified. Using center of mass equations (as shown in FIG. 4), with appropriate substitution of the DI values for the point-mass values, the location of damage is determined. These equations are adjusted slightly in the case of a different number of transducers or a non-uniformly spaced array of transducers, in a manner which would be apparent to those skilled in the pertinent art.

As in all statistical detection schemes, the detection threshold value used in deriving the Cumulative Average Delta (CAD) statistic must be established according to a specified cost function which optimally maximizes detection probability while minimizing the false alarm rate. This threshold must account for all variation that normally occurs when the structure under evaluation is in its "undamaged condition" (e.g., due to structural loading and environmental conditions), and for changes due to damage smaller than the minimum flaw size which is desired to be detected.

Figure 5A:
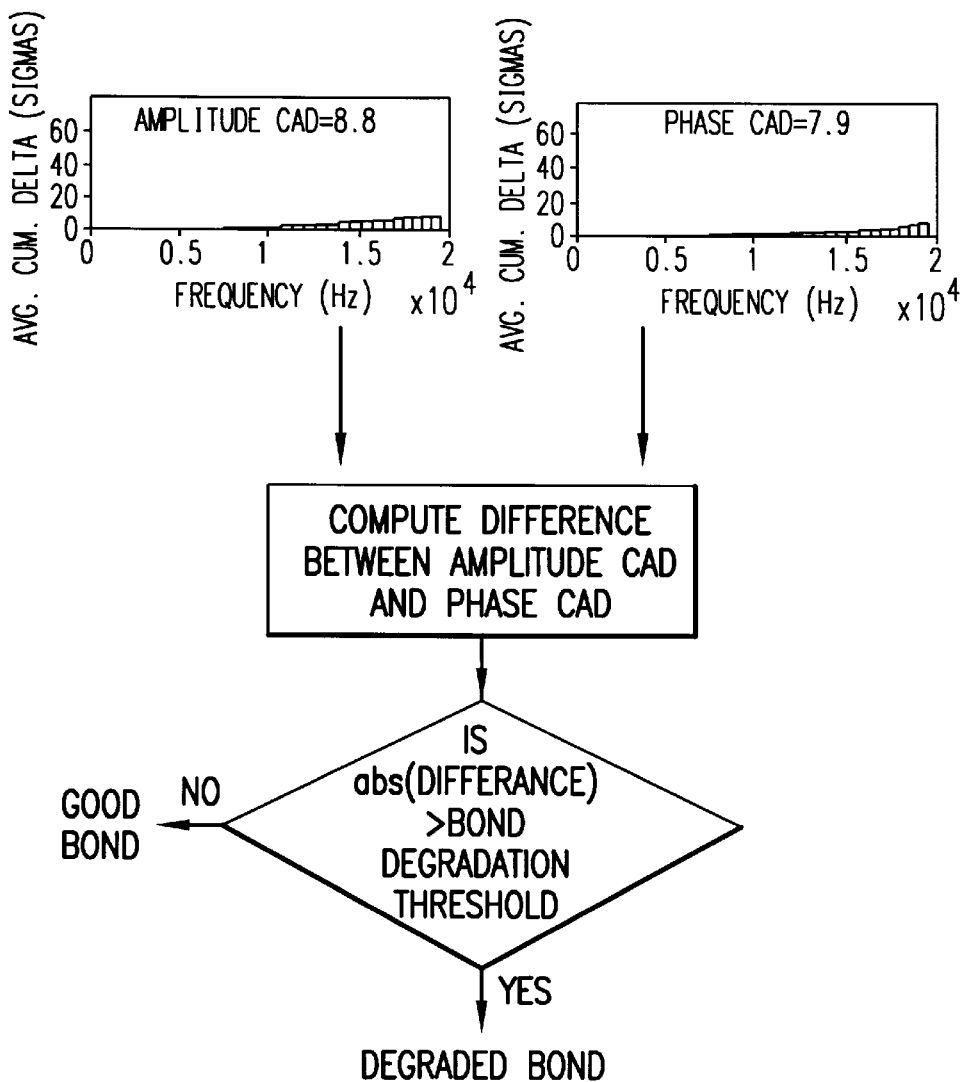
FIG. 5 depicts the processing logic which the ADI system of the present invention utilizes in detecting transducer bond degradation.
Figure 5B:
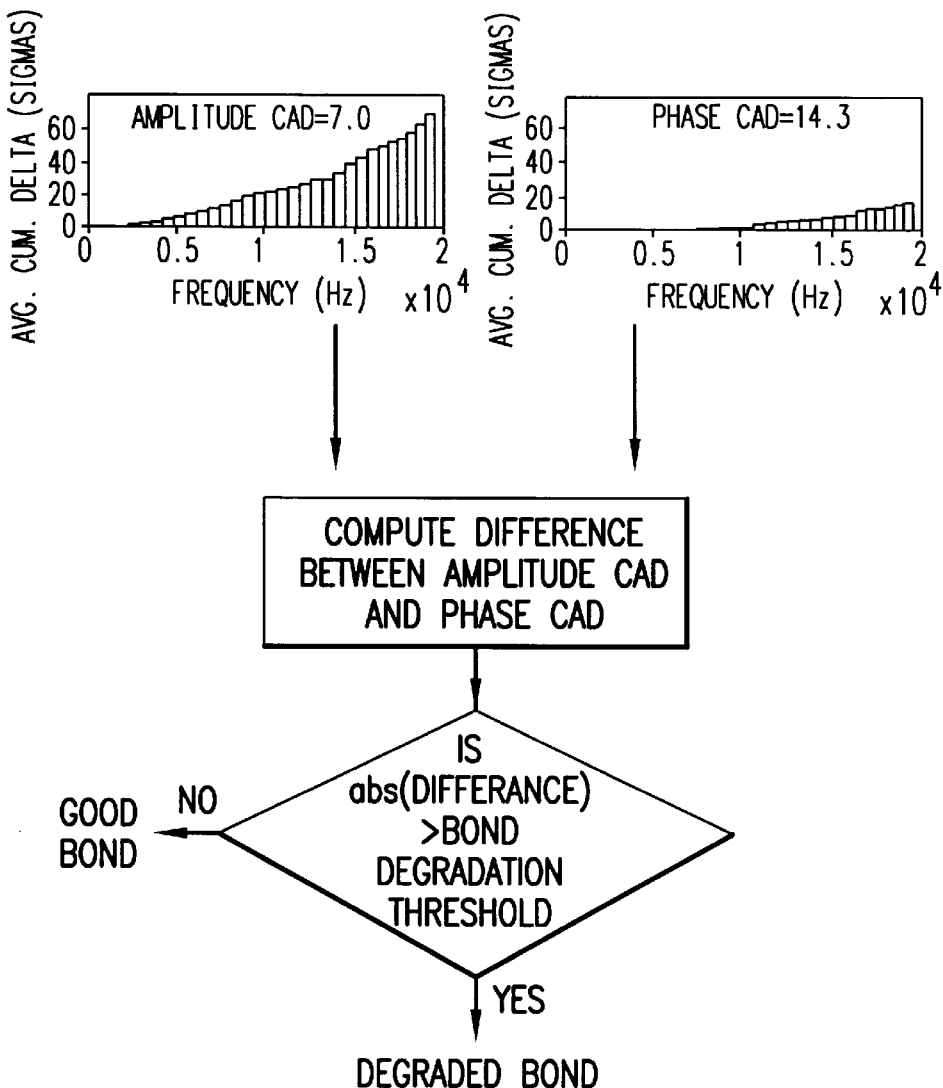

With reference now to FIG. 5, the process for detecting a degraded bond in a particular PZT transducer is illustrated. The underlying method involves computing the difference between the individual CAD values for phase and amplitude. If the difference does not exceed a predetermined threshold, which should be a relatively small percentage of the total CAD, then the bond is considered good. The two CAD values are then combined according to a weighted average based on empirical studies with the particular material, structure, and defect of interest. If no a priori information is available, a simple average will suffice. If the amplitude CAD exceeds the phase CAD by an amount greater than the threshold, the bond is considered to be degraded. Only the phase CAD should be used for further damage localization processing. This information should be used to set a maintenance code for repair of the bond if this is feasible.

EXPERIMENTAL LABORATORY SETUP

An experimental laboratory setup of the ADI system of the present invention was used to demonstrate the viability of the methodology of the present invention. The test article which was used for the experimental testing was a composite structural component (the flexbeam) of the MD-900 Explorer helicopter rotor system. The MD-900 flexbeam is a glass-epoxy composite structure which links the rotorblades to the hub and is housed inside the pitchcase. The flexbeam is a critical load-bearing structural component on the MD-900, since the loads from the blades are transferred to the hub and the rest of the rotorcraft through these components. Since the flexbeams are composite structures, delamination damage is a major concern.

In the experimental laboratory setup, two different actuator/sensor instrumentation configurations were used and experiments conducted using both configurations. In both experiments, the flexbeam was suspended in a free-free boundary condition. The first actuator/sensor instrumentation configuration is depicted in FIG. 6, and the second actuator/sensor instrumentation configuration is depicted in FIG. 7.

Figure 6:
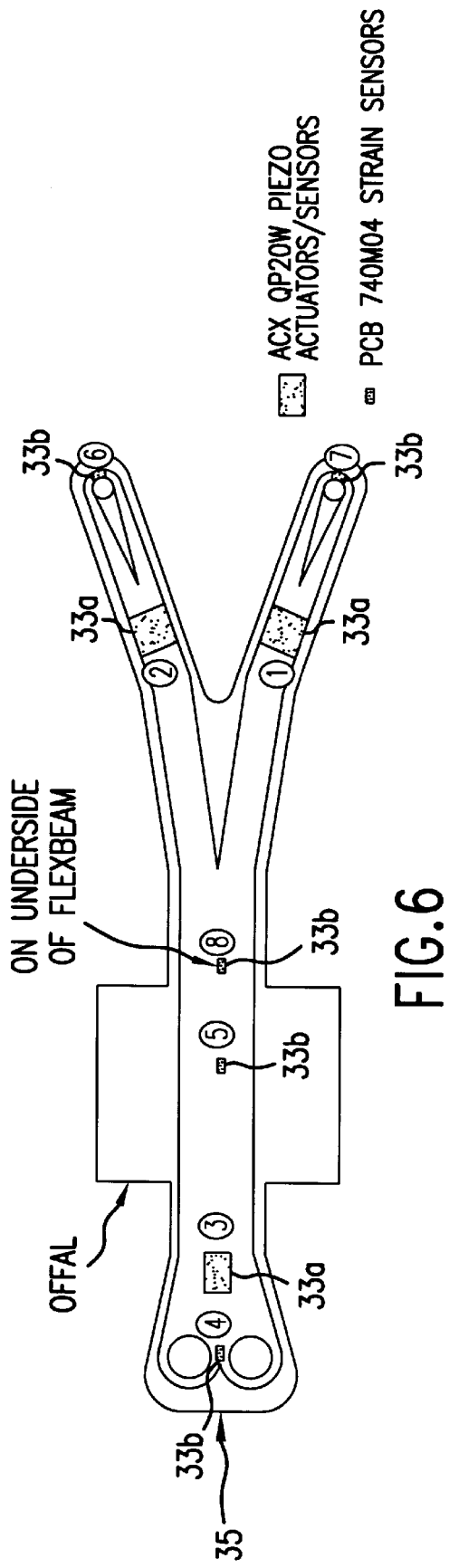
FIG. 6 is a graphical illustration of a first actuator/sensor instrumentation configuration employed in the experimental laboratory setup of the ADI system of the present invention.

As can be seen in FIG. 6, in the first actuator/sensor instrumentation configuration, eight PZT transducers were utilized, three for both actuation and sensing (33a), and five for sensing only (33b). This configuration was used for testing ADI system performance for evaluation of notch damage in the offal (scrap) region of the flexbeam 35.

Figure 7:
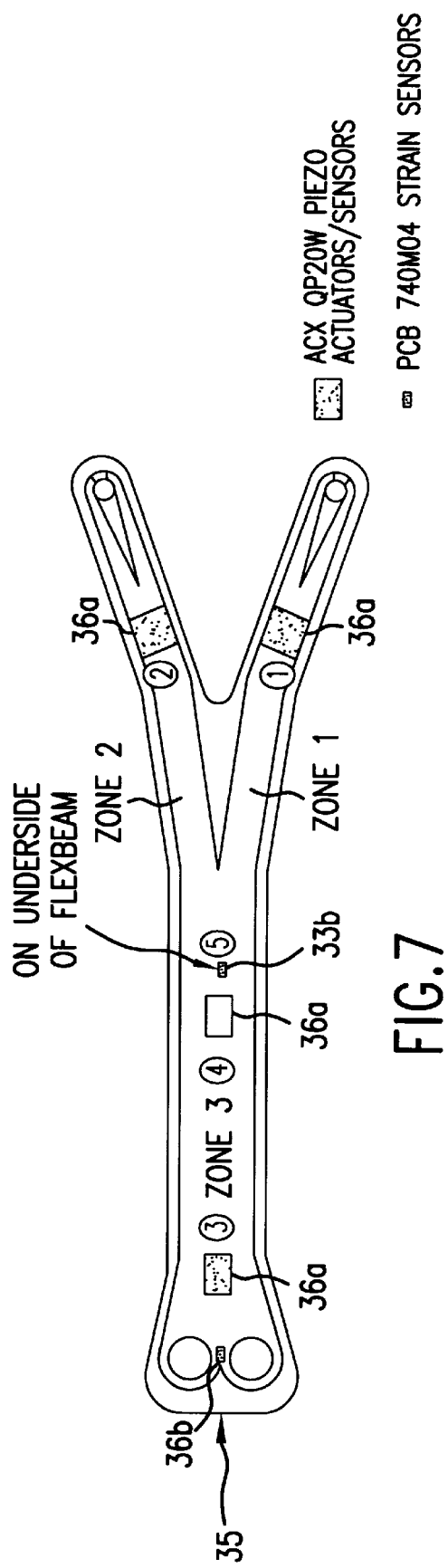
FIG. 7 is a graphical illustration of a second actuator/sensor instrumentation configuration employed in the experimental laboratory setup of the ADI system of the present invention.

As can be seen in FIG. 7, in the second actuator/sensor instrumentation configuration, five PZT transducers were utilized, four for both actuation and sensing (36a), and one for sensing only (36b). This configuration was used for testing ADI system performance for evaluation of delamination damage of the flexbeam 35'. Three damage zones ("Zone 1, Zone 2, and Zone 3") were identified for evaluating the damage localization performance of the ADI system.

In both configurations, the transducers used for both actuation and sensing were the Active Control eXperts (ACX) QP20W QuickPack units, which each have dimensions of 2"×1.5"×0.03" and include two piezoelectric thin wafers stacked on top of each other. Each QP20W transducer can provide the source when excited, and can also act as a sensor when not actuating. The transducers used for sensing only were PCB 740M04 piezoelectric crystal strain sensors, which are low profile strain sensors (measuring $\frac{5}{8}"\times\frac{3}{16}"\times\frac{1}{16}"$) that require a constant current source for operation. All of the transducers were bonded to the surface of the flexbeam using Mbond 200, which is an adhesive used by McDonnell Douglas Aerospace for the bonding of conventional foil strain gauges.

EXPERIMENTAL RESULTS

This section describes the experimental results obtained with the ADI system in detecting, localizing, and assessing the severity of damage inflicted on the flexbeam article in the laboratory. The first section describes the results of the notch damage studies and the second section describes the results of the delamination damage studies.

Notch Damage Results

The goal of the notch damage studies was to utilize the offal (scrap) region of the flexbeam for damage creation and detection before it was trimmed off. In this way, a preliminary evaluation of the ADI system performance could be made before beginning the delamination studies. To initiate damage and simulate crack growth in the offal region, notches were cut into the wide portion of the offal using a cutting blade and a Dremel tool. The first notch was cut into the offal about ¼", at the base end of the wide offal region. This notch was then extended to ½" in the offal from the edge towards the actual part. Subsequently, twenty-six successive notches were cut into the wide offal region, ¼" deep and ¼" apart moving towards the "Y" end of the flexbeam. The final notch was then extended fully through the offal to the edge of the flexbeam.

Figure 8A:
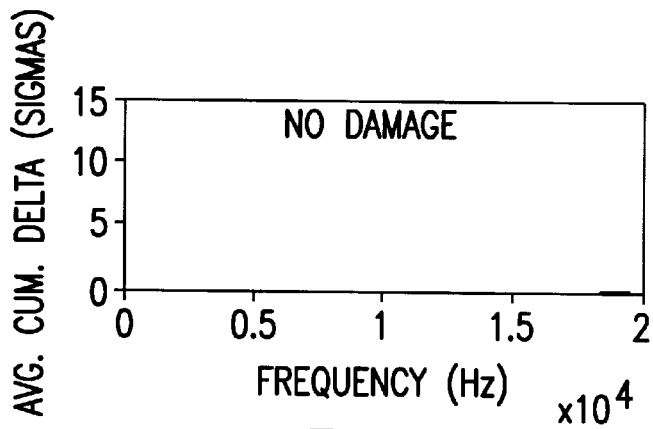
FIGS. 8A, 8B, and 8C are graphs depicting the Cumulative Average Delta spectrum from actuator 3 to sensor 1 of the first actuator/sensor instrumentation configuration employed in the experimental laboratory setup of the ADI system of the present invention, for the cases of no damage, one notch, and all notches, respectively.
Figure 8B:
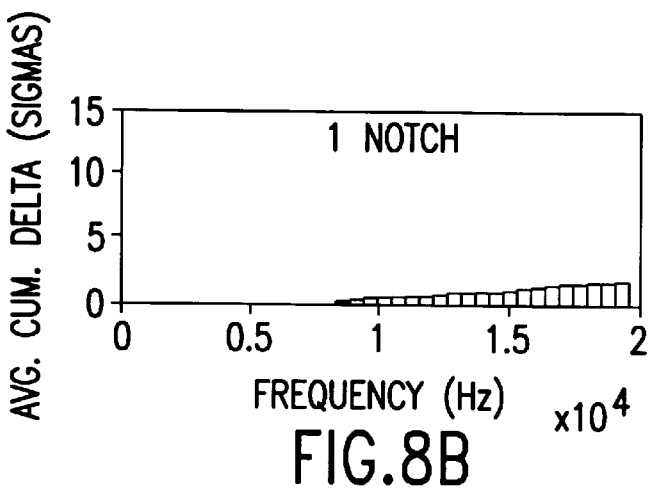
Figure 8C:
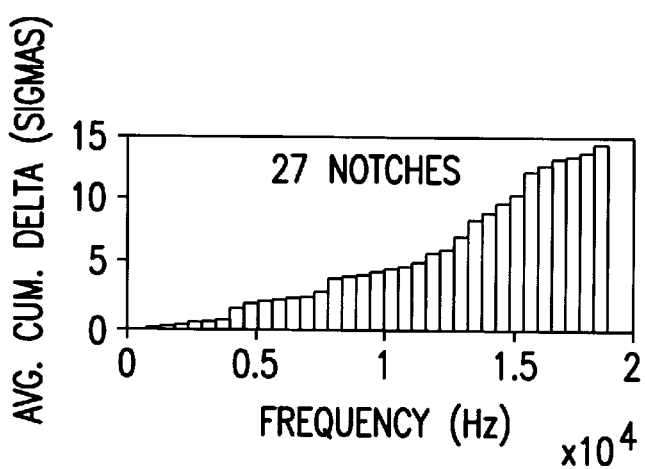
Figure 9:
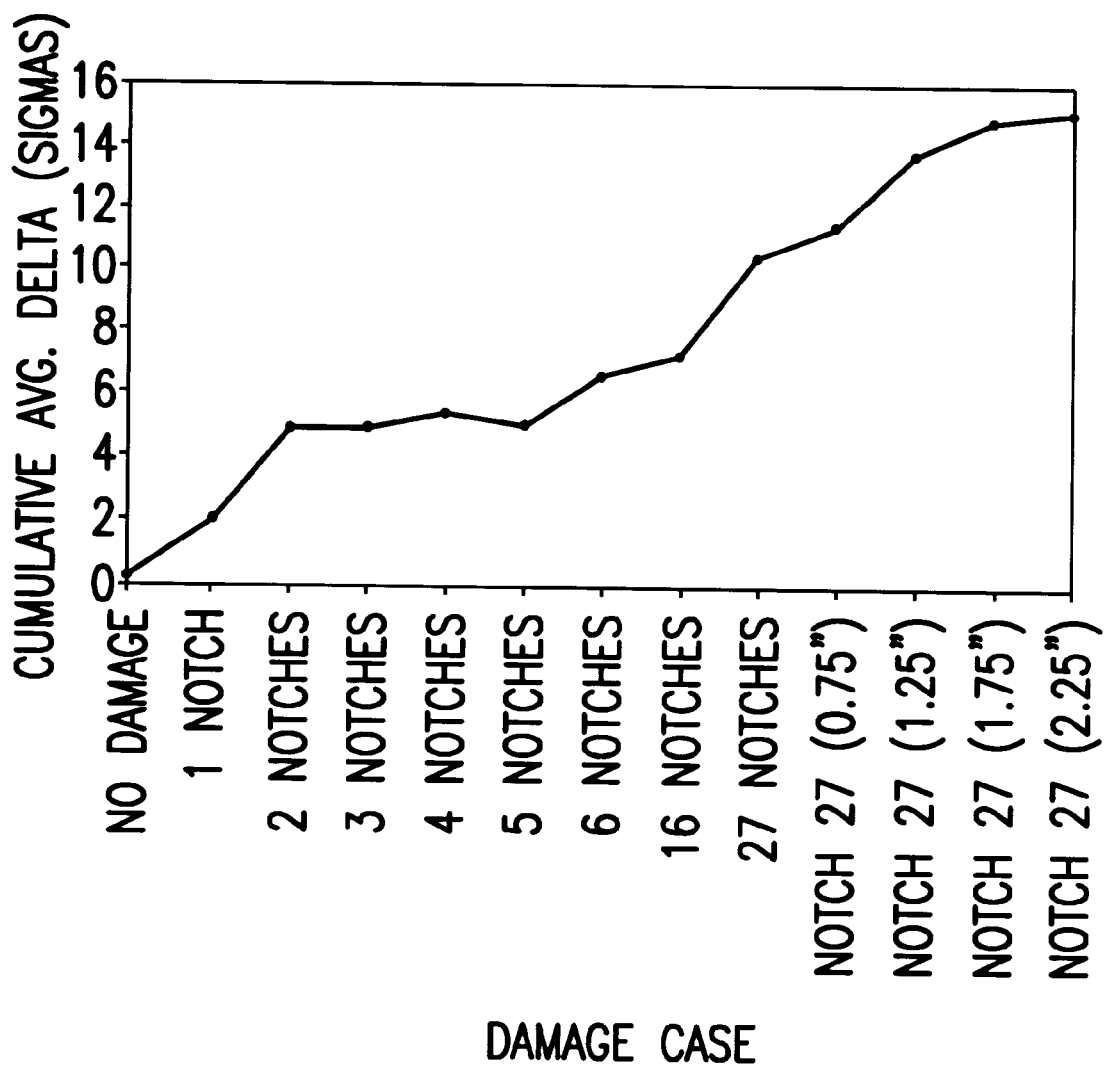
FIG. 9 is a graph which plots the overall Cumulative Average Delta value for the actuator/sensor pair considered in FIGS. 8A–8C for all notch damage cases considered in FIGS. 8A, 8B, and 8C; and, FIGS. 10A–10D are graphs of the Cumulative Average Delta Statistics for actuator #4 with respect to each of the sensors 1, 2, 3, and 5, respectively, of the second actuator/sensor instrumentation configuration employed in the experimental laboratory setup of the ADI system of the present invention, for edge delamination damage.
Figure 10A:
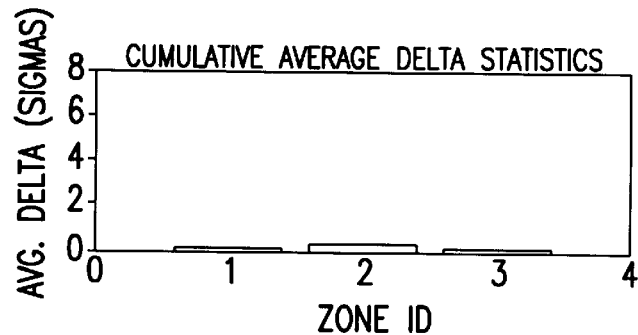
Figure 10B:
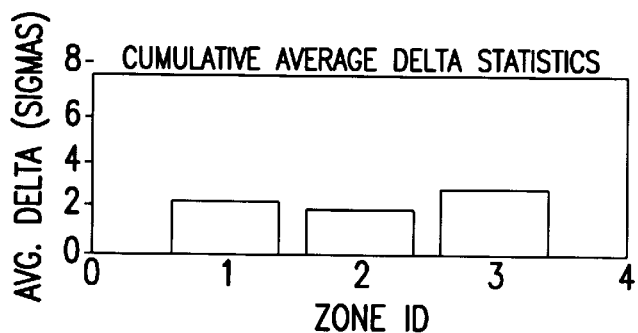
Figure 10C:
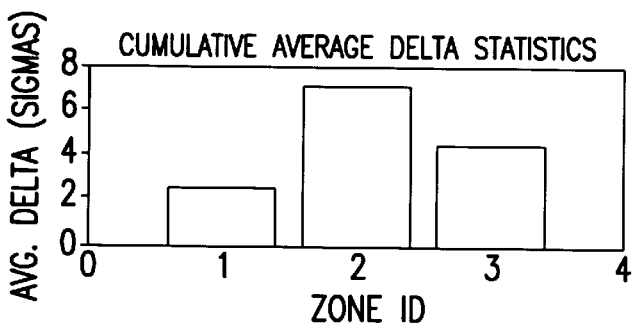
Figure 10D:
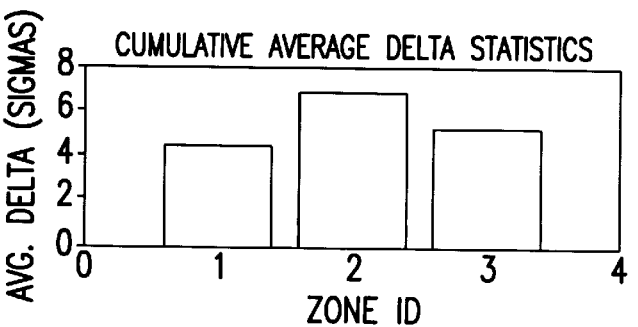

The ADI system was able to detect the notches quite easily. The Cumulative Average Delta spectrum from actuator 3 to sensor 1 for no damage, one notch, and all notches are presented in FIGS. 8A, 8B, and 8C, respectively. FIG. 9 plots the overall Cumulative Average Delta value from this actuator/sensor pair for all notch damage cases. A general trend of increasing Cumulative Average Delta values with progressively greater notch damage is obvious from this plot. These results clearly illustrate the ability of the ADI system to detect the presence of damage and to assess its severity. The localization performance of the ADI system was not evaluated here, but was evaluated in the delamination studies described below.

Edge Delamination Damage Results

After the notch damage analysis was completed, the large sections of offal were removed and the flexbeam was instrumented in the second actuator/sensor instrumentation configuration. Fifteen sets of data were collected over a time span of two weeks to generate a new set of baseline transfer functions. Three edge delaminations were then created in each damage zone of the flexbeam to evaluate both damage detection and damage localization performance of the ADI system. The delaminations were created by carefully driving a thin knife blade into the edge of the flexbeam to a depth of 0.25 inches. The delaminations in Zones 1 and 3 were considered to the smallest, with the delamination in Zone 2 being the largest. Subsequent ultrasonic inspection confirmed this. The delaminations in Zones 1 and 3 were about 0.5" deep by 1 " wide. The delamination in Zone 2 was approximately 0.75" deep by 1.75" wide.

The ADI system was able to easily detect and localize the delaminations, as is evidenced by the graphs of the Cumulative Average Delta Statistics for actuator #4 with respect to each of the sensors 1, 2, 3, and 5 depicted in FIGS. 10A–10D.

Internal (Impact) Delamination Damage Experiment

Low velocity impacts were used to induce delaminations at two locations on an MD Explorer flexbeam test article. At each site, three internal (impact) delaminations were created by dropping a 2.9 pound weight with a 0.5" diameter point from heights of 1–3 feet. First, a small delamination was created and an ultrasonic inspection was performed to determine the size of the delamination. This process was repeated until a desirable delamination size was achieved. Once the desirable size was achieved, data was collected on the flexbeam. The small delamination was then enlarged to produce the medium-sized delamination. The process of ultrasonically inspecting the flexbeam, inducing damage, and collecting data was repeated three times at each damage site, giving a total of six impact delaminations with diameters ranging from 0.5 to 1.25 inches. The frequency domain-based ADI system of the present invention was then proven to be extremely effective in detecting and localizing the impact-induced internal delamination damage. Perfect detection performance of 100% detection probability and zero false alarm rate was achieved for this limited data base. Very accurate localization was also achieved by the ADI system of the present invention.

Although the present invention has been described in detail hereinabove, it should be clearly understood that many variations and/or modifications of the basic inventive concepts taught herein which may appear to those skilled in the pertinent art will still fall within the spirit and scope of the present invention as defined in the appended claims.

For example, although it has been demonstrated that the ADI system (and method) of the present invention is capable of providing automatic damage assessment of composite structures of aerospace vehicles, it will be readily appreciated that it also has applicability to metallic structures, structural bonds and seals, machinery, and civil structures (e.g., bridges, buildings, power plants, etc.).

Some other applications of the ADI system and method of the present invention include, but are in no way limited to the following: (1) detection and localization of cracks, rivet line failures, and corrosion in metallic structures, (2) low cost damage detection and tracking for static and dynamic mechanical testing, (3) assessment of composite repair patch integrity, (4) detection of broken seals in low observable structural treatments, (5) detection of damage in rotating machinery and heavy machinery (e.g., mining equipment, earth movers, cranes, drilling rigs and platforms, etc.), (6) structural integrity monitoring for automobile manufacturing quality control (e.g., weld inspection, etc.), and (7) ice detection on aicraft structures (e.g., ice on aircraft wings).

What is claimed is:

1. A method for monitoring the structural health of a structure having a plurality of transducers, including a plurality of pairs of actuators and sensors, secured thereto, comprising the steps of:

exciting the actuators with broadband excitation across a prescribed frequency range, wherein each of the sensors produces an analog sensor signal in response to the excitation of the actuators;

digitizing the analog sensor signals to thereby produce digitized sensor signals;

computing a transfer function for each actuator/sensor pair using the digitized sensor signals;

comparing the magnitude of each computed transfer function with a baseline transfer function for the corresponding actuator/sensor pair; and, deriving a composite damage indication value for the structural health of the structure at the location of each actuator from the determined differences between the computed and baseline transfer functions for each actuator/sensor pair.

2. The method as set forth in claim 1, wherein:

at least one of the transducers comprises a transducer which is capable of both actuating and sensing; and, each of said at least one of the transducers comprises both an actuator and a sensor.

3. The method as set forth in claim 2, wherein the structure further has at least one further transducer which is capable of only sensing.

4. The method as set forth in claim 1, wherein the prescribed frequency range is 0 to 100 kHz.

5. The method as set forth in claim 1, wherein the broadband excitation comprises white noise excitation or chirp excitation.

6. The method as set forth in claim 1, wherein the computing step is performed by Fast Fourier Transform processing the digitized sensor signals.

7. The method as set forth in claim 1, wherein the baseline transfer function for each actuator/sensor pair is derived by obtaining a plurality of transfer function data sets for that actuator/sensor pair with the structure in an undamaged condition, then averaging the thusly obtained plurality of transfer function data sets for that actuator/sensor pair to produce an average transfer function data set for that actuator/sensor pair, and then computing a standard deviation of the baseline transfer function for each actuator/sensor pair based upon a statistical comparison of the plurality of transfer function data sets for that actuator/sensor pair with the average transfer function data set for that actuator/sensor pair.

8. The method as set forth in claim 7, wherein the computing a transfer function step includes the sub-steps of:

normalizing the determined differences between the computed and baseline transfer functions for each actuator/sensor pair by computing the number of standard deviations between the computed and baseline transfer function for each acuator/sensor pair, to thereby produce a transfer function deviation for each actuator/sensor pair expressed in terms of the number of standard deviations between the computed transfer function and the baseline transfer function for that actuator/sensor pair;

repeating the normalizing sub-step for each of a plurality of frequencies within the prescribed frequency range to produce a plurality of transfer function deviations over the prescribed frequency range;

integrating the transfer function deviations for each actuator/sensor pair over the prescribed frequency range, to thereby produce a cumulative delta value for each actuator/sensor pair; and, deriving the composite damage indication value for the structural health of the structure at the location of each actuator from the cumulative delta values.

9. The method as set forth in claim 8, wherein the transducers are each capable of both actuating and sensing, whereby those transducers which are actuating at a given time comprise actuators at that given time, and those transducers which are sensing at a particular time comprise sensors at that particular time.

10. The method as set forth in claim 9, wherein the structure further has at least one further transducer which is capable of only sensing.

11. The method as set forth in claim 8, further comprising the step of localizing damage to the structure by identifying the highest composite damage indication value.

12. The method as set forth in claim 8, wherein each composite damage indication value is indicative of a level of damage to a local region of the structure surrounding the corresponding actuator.

13. The method as set forth in claim 8, further comprising the step of windowed local averaging the transfer function deviation for each actuator/sensor pair prior to performing the integrating step, to thereby produce windowed local averaged transfer function deviations that comprise the transfer function deviations which are integrated in the integrating step.

14. The method as set forth in claim 1, wherein the computing step is performed by computing the magnitude of the analog sensor signals as a function of the frequency of the excitation.

15. The method as set forth in claim 1, wherein the computing step is performed by computing the magnitude and phase of the analog sensor signals as a function of the frequency of the excitation.

16. The method as set forth in claim 1, further comprising the step of comparing the phase of the computed transfer function for each actuator/sensor pair with the phase of the corresponding baseline transfer function for that actuator/sensor pair.

17. The method as set forth in claim 16, further comprising the step of discriminating between damage to the structure and damage to a bond between the transducers and the structure in response to the step of comparing the phase of computed transfer function for each actuator/sensor pair with the phase of the corresponding baseline transfer function for that actuator/sensor pair.

18. The method as set forth in claim 1, wherein the structure is a composite structure.

19. The method as set forth in claim 18, wherein the composite structure is a part of an aerospace vehicle.

20. The method as set forth in claim 1, wherein each of the transducers is a piezoelectric transducer.

21. The method as set forth in claim 1, wherein the structure is a metallic structure.

22. A system for monitoring the structural health of a structure having a plurality of transducers, including a plurality of pairs of actuators and sensors, secured thereto, comprising:

means for exciting the actuators with broadband excitation across a prescribed frequency range, wherein each of the sensors produces an analog sensor signal in response to the excitation of the actuators;

means for digitizing the analog sensor signals to thereby produce digitized sensor signals; and, means for computing a transfer function for each actuator/sensor pair using the digitized sensor signals, for comparing the magnitude of each computed transfer function with a baseline transfer function for the corresponding actuator/sensor pair, for determining the difference between the computed and baseline transfer functions for each actuator/sensor pair, and for deriving a composite damage indication value for the structural health of the structure at the location of each actuator from the determined differences between the computed and baseline transfer functions for each actuator/sensor pair.

23. The system as set forth in claim 22, wherein:

at least one of the transducers comprises a transducer which is capable of both actuating and sensing; and, each of said at least one of the transducers comprises both an actuator and a sensor.

24. The system as set forth in claim 23, wherein the structure further has at least one further transducer which is capable of only sensing.

25. The system as set forth in claim 22, wherein the prescribed frequency range is 0 to 20 kHz.

26. The system as set forth in claim 22, wherein the broadband excitation comprises white noise excitation.

27. The system as set forth in claim 22, wherein the computing means computes the transfer functions by Fast Fourier Transform processing the digitized sensor signals.

28. The system as set forth in claim 22, wherein the baseline transfer function for each actuator/sensor pair is derived by obtaining a plurality of transfer function data sets for that actuator/sensor pair with the structure in an undamaged condition, then averaging the thusly obtained plurality of transfer function data sets for that actuator/sensor pair to produce an average transfer function data set for that actuator/sensor pair, and then computing a standard deviation of the baseline transfer function for each actuator/sensor pair based upon a statistical comparison of the plurality of transfer function data sets for that actuator/sensor pair with the average transfer function data set for that actuator/sensor pair.

29. The system as set forth in claim 28, wherein the computing means further functions to normalize the determined differences between the computed and baseline transfer functions for each actuator/sensor pair by computing the number of standard deviations between the computed and baseline transfer function for each acuator/sensor pair, to thereby produce a transfer function deviation for each actuator/sensor pair expressed in terms of the number of standard deviations between the computed transfer function and the baseline transfer function for that actuator/sensor pair, to repeat the normalizing function for each of a plurality of frequencies within the prescribed frequency range to produce a plurality of transfer function deviations over the prescribed frequency range, to integrate the transfer function deviations for each actuator/sensor pair over the prescribed frequency range, to thereby produce a cumulative delta value for each actuator/sensor pair, and to derive the composite damage indication value for the structural health of the structure at the location of each actuator from the cumulative delta values.

30. The system as set forth in claim 29, wherein the transducers are each capable of both actuating and sensing, whereby those transducers which are actuating at a given time comprise actuators at that given time, and those transducers which are sensing at a particular time comprise sensors at that particular time.

31. The system as set forth in claim 30, wherein the structure further has at least one further transducer which is capable of only sensing.

32. The system as set forth in claim 28, wherein each composite damage indication value is indicative of a level of damage to a local region of the structure surrounding the corresponding actuator.

33. The system as set forth in claim 28, wherein the computing means performs windowed local averaging of the transfer function deviation for each actuator/sensor pair prior to integrating the transfer function deviations, to thereby produce windowed local averaged transfer function deviations which are subsequently integrated.

34. The system as set forth in claim 22, wherein the computing means computes the magnitude of the analog sensor signals as a function of the frequency of the excitation.

35. The system as set forth in claim 22, wherein the computing means computes the magnitude and phase of the analog sensor signals as a function of the frequency of the excitation.

36. The system as set forth in claim 22, wherein the computing means further compares the phase of the computed transfer function for each actuator/sensor pair with the phase of the corresponding baseline transfer function for that actuator/sensor pair.

37. The system as set forth in claim 36, wherein the computing means further discriminates between damage to the structure and damage to a bond between the transducers and the structure.

38. The system as set forth in claim 22, wherein the structure is a composite structure.

39. The system as set forth in claim 37, wherein the composite structure is a part of an aerospace vehicle.

40. The system as set forth in claim 22, wherein each of the transducers is a piezoelectric transducer.

41. A system for monitoring the structural health of a structure having a plurality of transducers, including a plurality of pairs of actuators and sensors, secured thereto, comprising:

a first section which excites the actuators with broadband excitation across a prescribed frequency range, wherein each of the sensors produces an analog sensor signal in response to the excitation of the actuators;

a second section which digitizes the analog sensor signals to thereby produce digitized sensor signals; and, a third section which computes a transfer function for each actuator/sensor pair using the digitized sensor signals, which compares the magnitude of each computed transfer function with a baseline transfer function for the corresponding actuator/sensor pair, which determines the difference between the computed and baseline transfer functions for each actuator/sensor pair, and which derives a composite damage indication value for the structural health of the structure at the location of each actuator from the determined differences between the computed and baseline transfer functions for each actuator/sensor pair.

42. The system as set forth in claim 41, wherein the baseline transfer function for each actuator/sensor pair is derived by obtaining a plurality of transfer function data sets for that actuator/sensor pair with the structure in an undamaged condition, then averaging the thusly obtained plurality of transfer function data sets for that actuator/sensor pair to produce an average transfer function data set for that actuator/sensor pair, and then computing a standard deviation of the baseline transfer function for each actuator/sensor pair based upon a statistical comparison of the plurality of transfer function data sets for that actuator/sensor pair with the average transfer function data set for that actuator/sensor pair.

43. The system as set forth in claim 42, wherein the third section further functions to normalize the determined differences between the computed and baseline transfer functions for each actuator/sensor pair by computing the number of standard deviations between the computed and baseline transfer function for each actuator/sensor pair, to thereby produce a transfer function deviation for each actuator/sensor pair expressed in terms of the number of standard deviations between the computed transfer function and the baseline transfer function for that actuator/sensor pair, to repeat the normalizing function for each of a plurality of frequencies within the prescribed frequency range to produce a plurality of transfer function deviations over the prescribed frequency range, to integrate the transfer function deviations for each actuator/sensor pair over the prescribed frequency range, to thereby produce a cumulative delta value for each actuator/sensor pair, and to derive the composite damage indication value for the structural health of the structure at the location of each actuator from the cumulative delta values.

44. The system as set forth in claim 43, wherein the transducers are each capable of both actuating and sensing, whereby those transducers which are actuating at a given time comprise actuators at that given time, and those transducers which are sensing at a particular time comprise sensors at that particular time.

45. The system as set forth in claim 44, wherein the structure further has at least one further transducer which is capable of only sensing.

* * * * *